United States Patent [19]

Vaillancourt

[11] Patent Number: 4,813,937
[45] Date of Patent: Mar. 21, 1989

[54] AMBULATORY DISPOSABLE INFUSION DELIVERY SYSTEM

[76] Inventor: Vincent L. Vaillancourt, 14 Bunyan Dr., Livingston, N.J. 07039

[21] Appl. No.: 162,041

[22] Filed: Feb. 29, 1988

Related U.S. Application Data

[63] Continuation of Ser. No. 860,581, May 7, 1986, abandoned.

[51] Int. Cl.$^4$ .......................................... A61M 37/00
[52] U.S. Cl. .................................. 604/131; 222/341;
128/DIG. 12; 604/135; 604/183; 604/222;
604/230; 604/236
[58] Field of Search .............................. 604/131–135,
604/184–186, 207, 208, 230, 136–139, 183, 214,
215, 216, 218, 222, 229, 236, 237, 238, 240;
128/DIG. 12; 222/341, 386

[56] References Cited

U.S. PATENT DOCUMENTS

| | | | |
|---|---|---|---|
| 1,799,463 | 4/1931 | Hein | 604/236 |
| 1,882,235 | 10/1932 | Spriggs | 604/135 |
| 2,725,877 | 12/1955 | Reiter et al. | 604/135 |
| 3,598,120 | 8/1971 | Mass | 604/208 |
| 3,831,602 | 8/1974 | Broadwin | 604/186 |
| 4,265,241 | 5/1981 | Portner et al. | 604/134 |
| 4,381,006 | 4/1983 | Genese | 604/135 |
| 4,386,929 | 6/1983 | Peery et al. | 604/132 |
| 4,612,010 | 9/1986 | Hamacher et al. | 604/218 |
| 4,636,197 | 1/1987 | Chu | 604/131 |
| 4,741,733 | 5/1988 | Winchell et al. | 604/132 |

FOREIGN PATENT DOCUMENTS

81/02523 9/1981 PCT Int'l Appl. ................ 604/140

Primary Examiner—John D. Yasko
Assistant Examiner—Mario Costantino
Attorney, Agent, or Firm—Kenyon & Kenyon

[57] ABSTRACT

There are depicted two embodiments of an ambulatory disposable infusion delivery system in which fluid (drug) is fed to a substantially transparent receiving and retaining housing which has indicia markings conventionally applied to indicate quantity. The inflow of fluid causes an elastomeric member attached to a piston, which is slideable in a bore in this housing, to be moved, thus stretching this member. This tension provides an energy source (force) to push the fluid out of the bore when the connected tubing line is opened. The housing is provied with a discharge fluid conduit and a restrictor controlling the rate of flow. In both embodiments, the housing has a barrel with a substantially constant bore. The slideable piston in this bore has a resilient outer portion with at least two ribs providing sealing action while having a low coefficient of friction. The front wall of the housing may be curved or straight and provides a fluid outlet as well as an aperture in which one end of a stretched elastomeric member is secured. The other end of this stretched member is secured to the slideable piston. Filling of the housing may be through a one-way valve or resilient plug. The controlling restrictor may be mounted and secured in the discharge tubing. This tubing may include a luer lock connector.

25 Claims, 2 Drawing Sheets

AMBULATORY DISPOSABLE INFUSION DELIVERY SYSTEM

This is a continuation of application Ser. No. 860,581, filed May 7, 1986, now abandoned.

BACKGROUND OF THE INVENTION

FIELD OF THE INVENTION

With reference to the field of art as established in and by the United States Patent Office, this invention is believed to be found in the general class entitled "Surgery" and, more particularly, relates to an improvement in a disposable infusion delivery system that provides a constant delivery rate to a patient.

DESCRIPTION OF THE PRIOR ART

Many infusion systems have been proposed and sold for the dispensing of drugs into a patient. With few exceptions, these systems contain both reusable (hardware components) and disposable parts. These systems include, for the most part, electrical components, with their attendant costs and limitations. The system as shown and described in the present application has an infusion delivery system that does not use or utilize electrical or electronically-related components, and this new and novel delivery system is completely disposable after a one-time use.

The delivery of medication may include a catheter as the vascular access device or dispensing may be through a needle penetrating an implanted vascular access port which in turn is connected to a blood vessel using an internal catheter. The delivery of this medication includes a small receiving means and the delivery is through a catheter-vascular access port at a constant rate for an extended and determined period of time. Devices of this type are preferably light in weight and pocket accessible. The devices are normally disposed at completion of the infused dosage of medication for convenience, elimination of mixed drugs, and minimizing contamination. At present, most, if not all, disposable ambulatory medicator infusion devices employ an elastomeric bladder which is caused to be expanded as the drug is fed or otherwise flows into the bladder. The delivery is dependent upon the capability of the bladder to expand and contract. Among the issued U.S. patents showing or employing bladders as a means of storage and contraction to provide expulsion while providing pressure is No. 3,486,539 to JACUZZI, as issued Dec. 30, 1968. This dispensing device anticipates filling a bladder through a front-connected needle with a flow metering restrictor. U.S. Pat. No. 3,993,069 to BUCKLES et al, as issued Nov. 23, 1976, shows an expansible elastomeric bladder. This patent also has a separate flow-control device and the assembly includes this outer flow restrictor. U.S. Pat No. 4,318,400 to PEERY et al, as issued Mar. 9, 1981, also has an elastomeric bladder-powered infuser and a tubular case enclosure to prevent excessive expansion of the bladder. Drugs are fed through a needle and syringe to the bladder through a resilient plug at the rear of the device. U.S. Pat. No. 4,386,929 was also issued to PEERY et al on June 7, 1973, and is very similar to and is a continuation of U.S. Pat. No. 4,318,400 noted above. U.S. Pat. No. 4,419,096 to LEEPER et al, as issued on Dec. 6, 1983, showed apparatus very much like those to PEERY, noted above, but with an added lumen and bulbar filler portions to establish the contracted shape of the elastomeric bladder when the contents are, or substantially are, expelled.

SUMMARY OF THE INVENTION

Briefly, the invention provides an ambulatory infusion device or pump which includes a housing for a fluid, a piston which is slidably mounted in the housing and an elastomer member connected to and between the piston and the housing to stretch in response to movement of the piston during filling of the housing with a fluid and to impose a force on the piston after filling for expelling the fluid through an outlet aperture.

The infusion device is and it does provide, a small, lightweight cylindrical apparatus which is filled with fluid through a delivery device such as a hypodermic needle attached to a syringe and/or a pressurized container. The inflow of fluid causes a slideable piston to move rearwardly in a tubular barrel and elongate an elastomeric member. In this manner, energy is stored which is subsequently used to deliver this same fluid to an attached connector device to a patient's previously inserted catheter. This fluid is delivered at a predetermined rate of flow governed by the force provided by the stretched resilient member. This rate is thus predictable with a determined restrictor size.

The infusion device is sized to be carried inconspicuously on the patient's body. This low-cost infusion device allows it to be used as a disposable product so contamination, cleaning and resterilization problems are not present. The flow of stored fluid is self-regulated without constant monitoring. The fluid can be observed to determine volume remaining or released, clarity of drug (contamination not present).

One embodiment, a sliding piston is carried in a tubular chamber of a housing of selected length. The rear of this tubular housing may be closed by a cap to prevent contamination during filling and, when used, having a small aperture or air vent to prevent the development of negative pressure. The forward end of this housing is conected to a tubing set which includes means for injecting (infusing) drugs/fluids into a delivery system leading to the patient. An ingress means, such as a resilient plug, is provided for the insertion of the fluid (drug) into the tubing chamber, and with the fluid inflow the slideable piston is moved toward the rear of the chamber. This piston is connected at its forward end to an elastomeric strand member, preferably a rubber tube, which provides the compression force (rubber tube in tension) to draw the piston toward and to the front end of the chamber.

The product of the present invention is easily made and assembled. The interface between the elastomeric component and drug is minimal when compared to above-known bladder-type devices, thereby reducing the potential for extractables. The interior chamber between the piston and an end wall of the housing, unlike bladder products, can and does go toward a zero volume since the elastomeric member is preloaded (tensioned). The barrel in which the drug is carried is a see-through product in which medications may be, and usually are, observed prior to and during infusion. This visual potential allows the user to detect contamination, color changes, etc. The leading edge of the piston may be used as a measuring means (similar to present use in disposable syringes) to measure accurately the quantity of medication infused.

This delivery tubing conventionally has a connector by which a disconnect is achieved with a minimum effort, permitting replacement of the device after a one-time use. This discharge tubing from the device usually includes a luer lock hub connector which may include a filter and flow-control restrictor. In use, the fluid to be injected is flowed into the chamber through a one-way valve and/or injection port. The inflow of fluid under pressure into the chamber causes the piston to move rearwardly as this fluid fills the chamber. The rubber tube that supplies the compressing force is stretched (placed under tension) until the chamber is filled with the desired amount. The injection port is then closed. The device is primed by cracking the outlet female luer adapter, with the storage unit height being lower than the outlet. This device is not connected to the patient for a constant infusion delivery.

The infusion device is made for a patient to wear inconspicuously (usually under clothing) and is silent in use and, except for a connection to the catheter in the patient, is entirely self-contained. The intravenous feeding is at a controlled rate, with no adjustment required, and permits this device to be used in and with outpatient care. The administration of fluid through this infusion device is continuous and rate-controlled, so a steady flow is provided to the patient. The delivery rate of infusion fluid is dependent upon the force developed by the stretched elastomeric member which is in tension in combination with the restrictor size. These two parameters determine the fluid delivery rate.

It is anticipated that the device or system will hold about two to sixty cc.s of drug concentrate or mix, and as a fluid be dispensed through the connected tubing to a catheter/vascular access means in the patient. This delivery is at a constant rate for a period of time. As this device is very lightweight and small, the patient is not restricted but may be ambulatory. As this tubular housing is anticipated to be made of substantially transparent materials, the patient may visually ascertain when the fluid has been delivered, how much has been delivered as an infused dosage, and, when desired or empty, disconnected and discarded. A new device may then be connected to again provide a desired constant flow infusion.

This system or device is particularly useful for fluids used in chemotherapy, diabetes, pain relief and other drugs which exhibit a therapeutic effect through constant rate infusion. This system also may be used as a replacement of syringe pumps for home therapy wherein the need for such pumps is indicated. This system or device obviates the need for training and manipulating such pumps. The device, as to be hereinafter shown and described, provides a system that essentially is pre-assembled, requires minimal training, no technical skills, and is self-regulating. The system is tamper-proof in that once a satisfactory hook-up is made, there is no means for the patient to violate the system without the violation's becoming known.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of an ambulatory disposable infusion delivery system as adopted for use in the controlled delivery of medication and showing a preferred means for constructing the device and its use. These specific embodiments have been chosen for the purposes of illustration and description as shown in the accompanying drawings wherein:

BRIEF DESCRIPTION OF THE DRAWINGS

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

EMBODIMENT OF FIGS. 1 THROUGH 5

Figure 1:
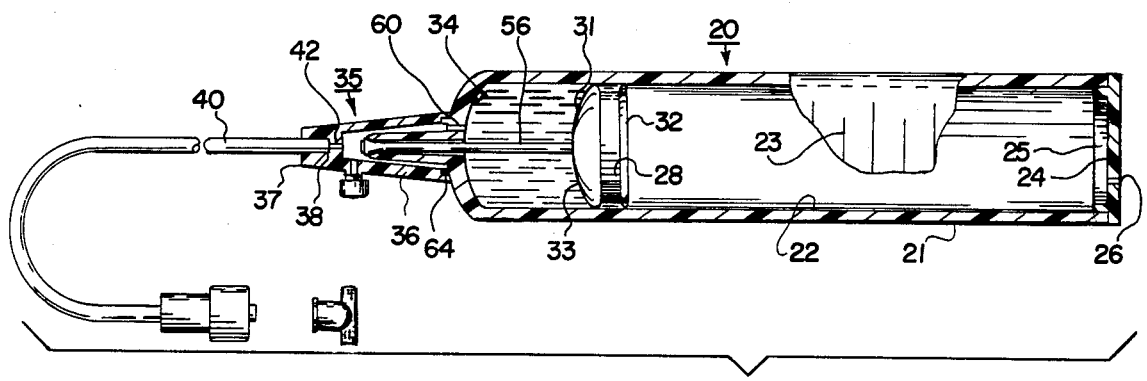
FIG. 1 represents a side view, partly in section and partly diagrammatic, and showing one embodiment of a disposable infusion delivery system and showing a flexible tubular means for deliverying fluid to a catheter.

Referring next to the drawings and the device illustrated therein, this system as assembled for use has an outer rigid cylindrical housing, generally identified as 20 to define a tubular chamber. This housing is usually molded of a transparent or translucent plastic, with the interior of the barrel 21 providing a relatively constant bore or diameter 22. This housing 20 is contemplated as having idicia 23 to indicate the fluid volume. These indicia may be molding rings, applied painted lines and/or numbers that are conventionally provided with syringes and like housings. A precise showing of graduations of indicia 23 differs with each device, as volume and desired flow rate are particular with each such device. For example, insulin has many differing dosages, etc., and the syringes used therewith have differing indicia. In the two embodiments shown and described, the internal structures are shown to more clearly illustrate the use and construction thereof. The fragmentary illustration in FIG. 1 is representative of conventionally-applied indicia. The rear or open end of barrel 21 may be closed with a cap 24 having a skirt 25 that is a snug fit within bore 22. A vent or small aperture 26 is formed in and through this cap, with this aperture 26 allowing air to enter the interior of the barrel 21 and preventing development of negative pressure as piston 28 is slid back and forth.

Figure 3:
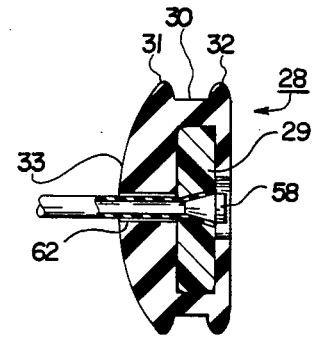
FIG. 3 represents an enlarged sectional side view showing this same tubing with its other end secured in and to a slideable piston.

This piston 28 is shown in greater detail in FIG. 3. This piston has a core 29 of substantially stiff material, such as polypropylene plastic, which retains its conformation when the elastomeric member is stretched. A tire portion 30 has right and left ribs or rings 31 and 32 which are shaped and sized to provide a minimum of friction with the interior surface 22 of the barrel 21. These rings may be of Teflon (TM duPont) or polypropylenecoated coated rubber, silicone rubber, coated neoprene and the like, or may have a treated surface to provide minimum friction while providing a seal when and while sliding. The forward face portion of this piston is formed with a spherical shape 33 to match the interior spherical configuration of a wall 34 at the front end of the housing. The forward (left) end portion of the housing is molded so as to have two coaxial tubular portions extending from the wall 34. The outer portion is generally identified as 35 and has a tapered shell 36 with a closed end 37 in which is formed a circular recess 38 for the insertion and retention of a flexible tubing conductor 40. A small aperture 42 is shown in and through the closed end 37. This small aperture may provide the desired fluid flow capability or control. This aperture provides a fluid-flow path from the interior of outer portion 35 to the interior of tubing 40.

Figure 4:
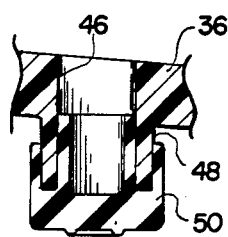
FIG. 4 represents an enlarged, very fragmentary, sectional side view showing a resilient plug mounted in a port formed in the extending portion of the housing nose portion and providing puncturing means for a hypodermic needle.
Figure 2:
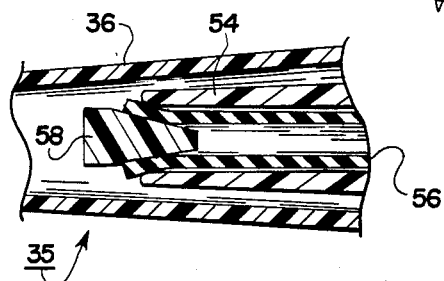
FIG. 2 represents an enlarged sectional side view of a forward extent of resilient tubing and a plug retainer for one end of this tubing.

In this outer tapered portion 36 is molded or formed a small communicating hole or aperture 46 see FIG. 4 and, for the convenience of mounting and positioning, there is shown a collar portion 48 also formed as this tapered portion 36 is molded. A resilient plug 50 is mounted in this collared portion and aperture 46. This plug provides a resilient seal which may be pierced by a needle from a syringe, not shown. Interior of tapered shell 36 is another and shorter tubular member 54 which may be integral with the molding of the barrel 21. As depicted, this member is tubular in configuration and has its outward (left) end formed with a taper to receive and retain a short length of rubber or other elastomeric tubing, identified as 56. This tubing 56 is secured coaxially in this tubular member 54 by a tapered plug 58. It is to be noted that in the integral wall portion between tapered shell 36 and tubular member 54 is a plurality of through holes 60. These holes provide fluid pathways from the interior of the housing and the cavity between shell 36 and member 54. The piston 28 is likewise provided with a through hole or aperture 62 (see FIG. 3) sized and adapted to receive the other end of tubing 56 coaxially, with another and like plug 58 securing this tubing 54 in the desired stretched condition. It is to be noted that for ease of manufacture and assembly, the tapered shell 36 is molded as a separate member and, as shown, has a shouldered joining, identified as 64, to provide a positive seating and securement. Sonic welding, cement or like means may be used and are contemplated so as to make shell 36 fluid-tight with housing 20 and with the desired strength capability.

Figure 5:
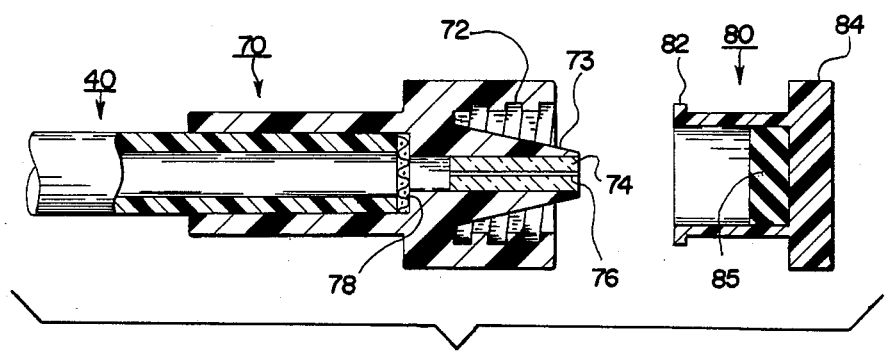
FIG. 5 represents an enlarged, and partly diagrammatic, sectional side view of luer lock connecting members.

In FIG. 5 there is depicted a luer lock device for connecting and disconnecting flexible tubing 40 to a catheter, not shown. The catheter is mounted in the patient to deliver medication in a controlled amount. As shown, a molded luer connection member 70 has threads 72 formed therein. The male tapered central portion, identified as 73, is shown with a mounted fluid restrictor 74 which has a predetermined through aperture 76. To the distal or left and at the end. of secured tube 40 is a filter disc 78. The mating winged luer cap connector is generally identified as 80 and has an eared portion 82 and a winged portion 84 providing manipulating means. This eared portion 82 is adapted to engage the threaded portion 72 and, when winged portion 84 is rotated, the male portion 73 is drawn into the connector 80 to close the aperture 76. The winged cap may be of rubber which is sufficiently resilient to act as or provide a resilient closure. It is also contemplated that a softer resilient member may be mounted in the cavity, identified as 85, to provide and insure that connector 70 is closed to a flow of fluid through conductor 40. The connector 70 and winged cap 80 utilized therewith are known and no patentable distinction is ascribed thereto.

EMBODIMENT OF FIG. 6 A THROUGH FIG. 8

There is also depicted an alternate construction providing an infusion delivery system adapted for high-speed automatic assembly. In this alternate embodiment, a housing, generally identified as 90, is a molding 91 and is formed with a substantially constant bore 92 to define a tubular chamber. The rear end of this molding may be closed by a cap 94 having a skirt portion 95 that is a snug fit within the bore 92. In this cap is also provided a vent or aperture 96 which allows atmospheric air to enter or that air within the barrel to be expelled so that development of negative or positive pressure within the housing does not occur when and with a sliding motion of a piston 98. This housing is formed with a forward wall 100 in which there are formed three through apertures.

A substantially central aperture is identified as 102 and is provided with an outwardly-extending collar portion having an internal configuration with a taper. Another aperture 104 is also formed with an outwardly-extending collar portion with a stepped bore and with the larger exterior bore sized to accept and retain the end of tubing 40. The other aperture is identified as 106 and is sized to accept and retain a one-way valve (not shown) or a resilient plug such as 50, shown in FIG. 4 above.

Figure 7:
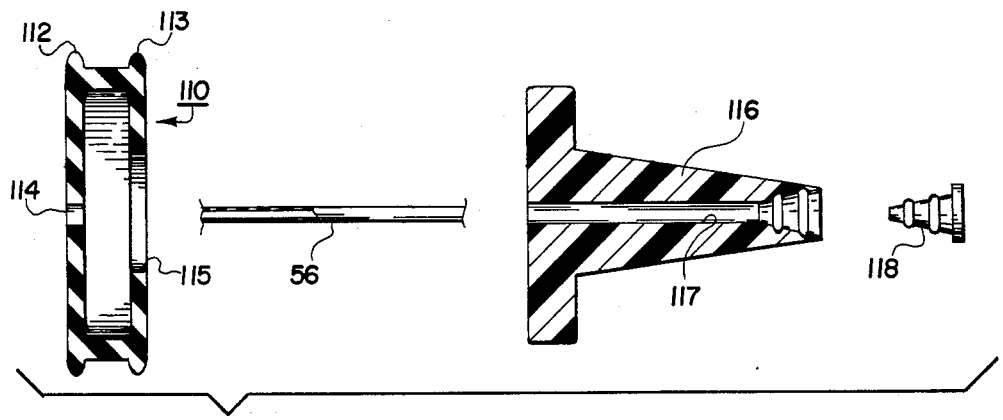
FIG. 7 represents an enlarged, and diagrammatic, expanded view of the slideable piston and a means of securing the end of a resilient tubing to same.

Piston 98, as depicted in the expanded view of FIG. 7, is an unassembled structure having an outer member 110 made of Teflon (TM duPont), coated rubber or silicone rubber, or a surface treated or coated to prevent sticking or sliding friction. This member 110 is provided with ribs or rings 112 and 113. Aperture 114 and enlarged aperture 115 are provided with and in this structure. A plastic molding 116 is made to fit the inside of the outer member 110. This molding has a through aperture 117, with the aperture formed with a small tapered portion adapted to receive and retain said plug when an elastomeric tubing 56 is brought into and through the aperture 117.

Figure 6A:
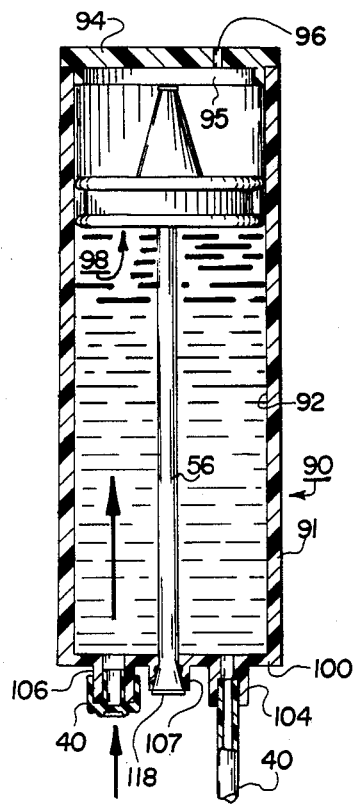
FIGS. 6 A, 6 B and 6 C represent sectional side views of an alternate cylindrical container, the slideable piston illustrted in three positions.
Figure 6B:
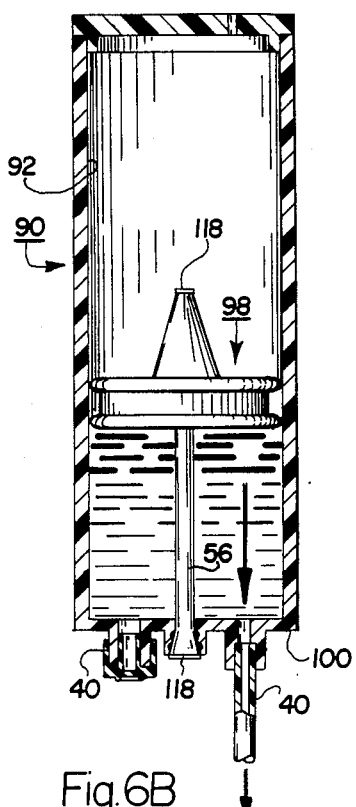
Figure 6C:
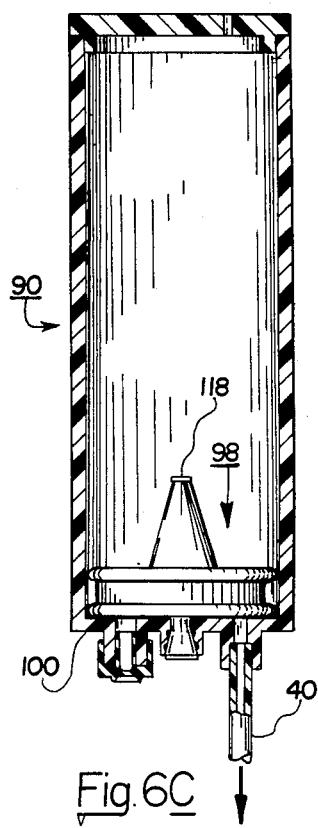
Figure 8:
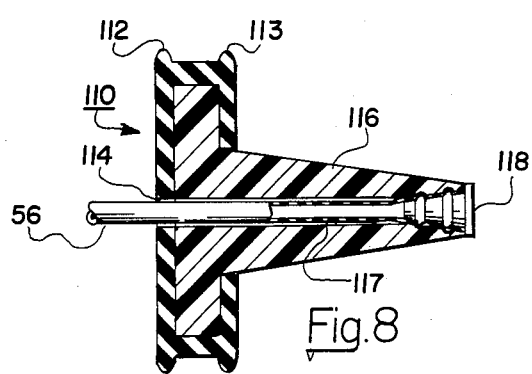
FIG. 8 represents a sectional side view showing the slideable piston of FIG. 7 in an assembled condition.

In FIG. 8 the piston assemby 98 is illustrated. The outer member 110 is shown with molding 116 inserted therein. The tubing 56 is inserted in and through aperture 117 and plug 118 is mounted in this end to secure and retain this tubing when and as the piston 98 is moved rearward. In FIG. 6 C the piston 98 is shown adjacent end 100. The tubing 40 is closed by the winged member 80 as in FIG. 5 above. With this conductor closed, a needle inserted through plug 50 and fluid (drugs) is flowed into the housing 90 to cause piston 98 to move rearwardly until the desired amount has been transferred. Tubing 56 is stretched to provide the desired constant tension as in FIG. 6 A. After the desired transfer (filling) has been achieved, connection to the patient is made and the piston, as moved by the stretched tubing 56, is caused to move toward end 100. The withdrawal of the needle causes the plug 50 to close and seal and, as shown in FIG. 6 B, the piston 98 is indicated as moving toward end 100. In FIG. 6 B the piston is shown midway, which is a position during filling and during the discharge of the fluid.

ASSEMBLY, USE AND OPERATION OF THE SYSTEMS OF FIGS. 1 THROUGH 8

The assembly of the system or device of FIGS. 1 through 5 anticipates high-speed, automatic or semiautomatic assembly of the several components identified above. The housing 20 is molded of an acceptable and inexpensive plastic, such as polypropylene, that is suitable for the drug or mixture to be used therein. The piston 98 is likewise made of materials suitable for short-term life. The sealing ribs or rings 31 and 32 on the added outer rim portion 30 are designed to provide a slideable seal for the period of intended use. If desired, the one-way valve (not shown) or resilient plug 50 may be deleted in favor of a stopcock or rubber injection site provided in the tubing member.

The tubing 56 is contemplated to be an elastomeric rubber or stretchable rubber-like material. Tubing is illustrated as retained by tapered plugs 58 (FIG. 2) or 118 (FIG. 7), which is a very positive securement means. A rubber band may also be utilized, but mechanical manipulation is more easily achieved with tubing which usually and more nearly provides a constant force through a given length of stretch. When the piston is adjacent the forward end of the housing, the tubing is stretched sufficiently to insure a constant force that will move the piston alongside this forward end of the housing. In the prior art devices, the elastomeric bladder, as provided, when it approaches a relaxed condition, loses a portion of its capability to return to its "as formed" condition.

In the embodiment of FIG. 6 A through FIG. 8, the front wall 100 is substantially flat so that the apertures 102, 104 and 106 are formed easily with and around pins extending from the mold core. As the cap 94 does not come in retentive contact with the fluid to the forward side of piston 98, this cap may be of a different material from barrel 90. The housing 90 or 20 is contemplated to be of a transparent or substantially transparent material so that the user or patient may visually view the drug for clarity, contamination, etc., quantity infused or remaining, and readily determine flow rate. A flow rate is established by the aperture 76 provided in the luer lock connector 70 (FIG. 5). A winged cap 80 is conventionally provided, but other means, such as clamps, are known to shut off flow. The connector tubing may be of small bore to minimize fluid hold-up. The interior lumen may be fluted or otherwise contoured so as to prevent a seal-off due to accidental kinkage of the connector tubing.

It is contemplated that this metered delivery may also have a flow delivery connected to the tubing 40 by which an added medication, such as a pain inhibitor (killer) may be selectively delivered to the patient.

The above-depicted and -described embodiments are believed to provide a basis for a method of assembly and use of an ambulatory disposable infusion delivery system and device. This method provides the following steps of:

molding a housing with a barrel having a substantially constant bore portion and with this bore having a rear and a front end;

positioning and mounting a slideable piston within said bore and forming on this piston outwardly-directed sealing means and providing attachment means for an elastomeric force member to said slideable piston;

forming a front closure portion in the housing and providing therein means for mounting and retaining a tubular fluid conduit through which fluid may be expelled from the interior of the housing and providing a second means for securing an elastomeric force member;

providing and stretching an elastomeric or rubber-like member as the force member and attaching one end to the slideable piston and forming in said front portion a retention means for said stretched member, and mounting a flow-control restrictor in the fluid-conduit path so as to precisely control the flow rate for the expelled fluid.

Terms such as "left," "right," "bottom," "top," "front," "back," "in," "out" and the like are applicable to the embodiments shown and described in conjunction with the drawings. These terms are merely for the purposes of description and do not necessarily apply to the position in which the infusion delivery system may be constructed or used.

While particular embodiments of the apparatus depicted for said infusion system have been shown and described, it is to be understood that the invention is not limited thereto and protection is sought to the broadest extent the prior art allows.

What is claimed is:

1. An infusion device comprising
a tubular housing for a fluid having an outlet aperture at one end for the fluid;
a piston slidably mounted in said housing; and
an elastomer member within said housing connected to and between said piston and said housing to stretch in response to movement of said piston during filling of said housing with a fluid about said member and to impose a force on said piston after filling for expelling the fluid through said outlet aperture.

2. An infusion device as set forth in claim 1 wherein said elastomer member is a tube.

3. An infusion device as set forth in claim 2 further comprising a first plug securing one end of said tube in an aperture in an end wall of said housing and a second plug securing an opposite end of said tube in an aperture in said piston.

4. An infusion device as set forth in claim 3 wherein each plug is resilient.

5. An infusion device as set forth in claim 1 which further comprises a restrictor defining said outlet opening for controlling the rate of flow from said housing.

6. An infusion device as set forth in claim 1 wherein said housing has a first projecting tubular portion secured to said elastomeric member and a second projecting tubular portion coaxial of said first projecting tubular portion and having a recess for receiving a flexible tubing in fluid communication with the interior of said second portion, said outlet located between said tubular portions to communicate with the interior of said housing for conveying fluid therethrough.

7. An infusion device as set forth in claim 6 further comprising an inlet aperture disposed in said second tubular portion for delivery of fluid into said housing.

8. An infusion device as set forth in claim 7 further comprising a one-way valve closing said inlet aperture.

9. An infusion device as set forth in claim 1 wherein said housing has a wall having said outlet aperture therein and having one end of said elastomeric member secured thereto.

10. An infusion device comprising
   a tubular housing for a fluid having a wall at one end with a first aperture therein and a second aperture for expelling fluid therefrom;
   a piston slidably mounted in said housing and having an aperture therein;
   a stretchable rubber tubing extending through said first aperture in said wall and through said aperture in said piston;
   a first plug mounted in one end of said tubing to secure said end to said wall in friction fit relation; and
   a second plug mounted in an opposite end of said tubing to secure said opposite end to said piston in friction fit relation.

11. A infusion device as set forth in claim 10 wherein each plug is tapered.

12. An infusion device comprising
   a tubular housing having a front wall having an inlet aperture for entry of a fluid and an outlet aperture for expelling fluid therethrough;
   a piston slidably mounted in said housing; and
   an elastomeric member connected to and between said wall and said piston within said housing to stretch in response to filling of a fluid into said housing through said inlet aperture and about said member and to impose a force on said piston after filling for expelling the fluid from about said member through said outlet aperture.

13. An infusion device as set forth in claim 12 wherein said elastomer member is a rubber tubing.

14. An infusion device as set forth in claim 12 which further includes a one-way valve in said inlet aperture to provide a fluid flow path into said housing for filling a chamber between said piston and said front wall with fluid.

15. An infusion device as set forth in claim 12 wherein said housing includes a pair of coaxial tubular portions extending from said wall with said apertures therebetween, an inner one of said portions receiving one end of said elastomer tubing in secured relation and an outer one of said portions having an aperture in fluid communication with the interior of said outer portion for communicating with a tubing conductor.

16. An infusion device as set forth in claim 15 which further includes a one-way valve in said outer tubular portion to provide a fluid flow path into said housing.

17. An infusion device as set forth in claim 12 wherein said front wall of said housing includes a third aperture receiving one end of said elastomer member in sealed and secured relation coaxially of said piston.

18. An infusion device as set forth in claims 12 wherein said piston includes a resilient ring-like member having a plurality of ribs for sealing engagement with said housing and a stiffner core within said ring-like member and receiving one end of said elastomer member in secured relation.

19. An ambulatory infusion pump comprising
   a housing defining a chamber and having a one-way valve for filling fluid into said chamber;
   a restrictor communicating with said chamber for controlling a rate of fluid flow from said chamber;
   a piston slidably mounted in said housing; and
   a stretchable elastomer member within said housing connected between said housing and said piston to stretch in response to movement of said piston during filling of said housing about said member with a fluid and to impose a force on said piston after filling for expelling the fluid through said restrictor.

20. An ambulatory infusion pump as set forth in claim 19 wherein said housing is of transparent material and includes indicia to indicate fluid volume.

21. An ambulatory infusion pump as set forth in claim 19 wherein said housing is tubular and includes a vented cap at one end for expelling air during filling of said chamber with fluid.

22. An ambulatory infusion pump as set forth in claim 19 which further comprises a flexible tubular conductor extending from said housing to provide a fluid flow path from said chamber and connected to said restrictor at a distal end thereof.

23. An infusion device comprising
   a tubular housing having a pair of coaxial projecting tubular portions at one end and a plurality of holes between said tubular portions communication with the interior of said housing for conveying fluid therethrough;
   a piston slidably mounted in said housing;
   a recess in an outer one of said projecting tubular portions for receiving a flexible tubing in communication with the interior of said second tubular portion; and
   an elastomer member connected to and between said piston and the inner one of said tubular portions to stretch in response to movement of said piston during filling of said housing with a fluid and to impose a force on said piston after filling for expelling the fluid through said holes and said recess.

24. An infusion device as set forth in claim 23 further comprising an inlet aperture disposed in said outer tubular portion for delivery of fluid into said housing.

25. An infusion device as set forth in claim 24 further comprising a one-way valve closing said inlet aperture.

* * * * *

UNITED STATES PATENT AND TRADEMARK OFFICE
CERTIFICATE OF CORRECTION

PATENT NO. : 4,813,937

DATED : March 21, 1989

INVENTOR(S) : Vincent L. Vaillancourt

It is certified that error appears in the above-identified patent and that said Letters Patent is hereby corrected as shown below:

In the Abstract, line 11, "provied" should read -- provided --.

Column 2, line 13, "is and it does provide, a" should read -- is a --.

Column 2, line 52, "the product of the present invention" should read -- the device --.

Column 5, line 68, "end. of" should read -- end of --.

Column 10, line 37, "communication" should read -- communicating --.

Signed and Sealed this

Twelfth Day of December, 1989

Attest:

JEFFREY M. SAMUELS

Attesting Officer  Acting Commissioner of Patents and Trademarks